(12) United States Patent
Walsh (10) Patent No.: US 10,159,587 B2
(45) Date of Patent: Dec. 25, 2018

(54) MEDICAL DEVICE DELIVERY SYSTEM WITH FORCE REDUCTION MEMBER

(71) Applicant: BOSTON SCIENTIFIC SCIMED, INC., Maple Grove, MN (US)

(72) Inventor: Kevin Walsh, Wellesly, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 233 days.

(21) Appl. No.: 14/996,879

(22) Filed: Jan. 15, 2016

(65) Prior Publication Data

US 2016/0206456 A1    Jul. 21, 2016

Related U.S. Application Data

(60) Provisional application No. 62/104,434, filed on Jan. 16, 2015.

(51) Int. Cl.
*A61F 2/06* (2013.01)
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC .................... A61F 2/966; A61F 2002/9517
USPC .............................................. 623/1.11–1.35
See application file for complete search history.

(56) References Cited

U.S. PATENT DOCUMENTS

| 3,613,684 | A | 10/1971 | Sheridan |
| 4,665,918 | A | 5/1987 | Garza et al. |
| 4,732,152 | A | 3/1988 | Wallstén et al. |
| 4,813,107 | A | 3/1989 | Cetrone |
| 4,906,232 | A | 3/1990 | Reynolds |
| 5,026,377 | A | 6/1991 | Burton et al. |
| 5,071,407 | A | 12/1991 | Termin et al. |
| 5,158,548 | A | 10/1992 | Lau et al. |
| 5,163,905 | A | 11/1992 | Don Michael |

(Continued)

FOREIGN PATENT DOCUMENTS

| EP | 0676936 A1 | 10/1995 |
| EP | 0684022 A2 | 11/1995 |

(Continued)

*Primary Examiner* — Amy R Weisberg
(74) *Attorney, Agent, or Firm* — Seager, Tufte & Wickhem, LLP (57) ABSTRACT

Medical devices and methods for making and using medical devices are disclosed. An example medical device may include a catheter shaft. The catheter shaft may include an inner member having a distal region and a deployment sheath disposed about the inner member. A stent may be disposed between along the distal region of the inner member. A handle may be coupled to the catheter shaft. An actuation mechanism may be coupled to the handle for proximally retracting the deployment sheath. The actuation mechanism may be designed to shift relative to the handle from a pre-deployment position, along an early deployment region, and along a full deployment region. The medical device may also include a force reduction member for applying a force to the actuation mechanism while the actuation mechanism is disposed along the early deployment region.

16 Claims, 8 Drawing Sheets

(56) References Cited

U.S. PATENT DOCUMENTS

| | | | |
|---|---|---|---|
| 5,201,757 A * | 4/1993 | Heyn | A61F 2/95 606/198 |
| 5,221,261 A | 6/1993 | Termin et al. | |
| 5,238,004 A | 8/1993 | Sahatjian et al. | |
| 5,346,471 A | 9/1994 | Raulerson | |
| 5,378,239 A | 1/1995 | Termin et al. | |
| 5,433,723 A | 7/1995 | Lindenberg et al. | |
| 5,443,907 A | 8/1995 | Slaikeu et al. | |
| 5,445,646 A | 8/1995 | Euteneuer et al. | |
| 5,496,277 A | 3/1996 | Termin et al. | |
| 5,534,007 A * | 7/1996 | St. Germain | A61F 2/95 606/191 |
| 5,571,135 A | 11/1996 | Fraser et al. | |
| 5,603,698 A * | 2/1997 | Roberts | A61F 2/95 604/104 |
| 5,662,703 A | 9/1997 | Yurek et al. | |
| 5,674,242 A | 10/1997 | Phan et al. | |
| 5,690,644 A | 11/1997 | Yurek et al. | |
| 5,695,499 A | 12/1997 | Helgerson et al. | |
| 5,702,364 A | 12/1997 | Euteneuer et al. | |
| 5,707,376 A | 1/1998 | Kavteladze et al. | |
| 5,713,860 A | 2/1998 | Kaplan et al. | |
| 5,733,267 A | 3/1998 | Del Toro | |
| 5,755,777 A | 5/1998 | Chuter | |
| 5,772,609 A | 6/1998 | Nguyen et al. | |
| 5,772,669 A | 6/1998 | Vrba | |
| 5,788,707 A | 8/1998 | Del Toro et al. | |
| 5,830,181 A | 11/1998 | Thornton | |
| 5,833,694 A | 11/1998 | Poncet | |
| 5,833,706 A | 11/1998 | St. Germain et al. | |
| 5,843,090 A | 12/1998 | Schuetz | |
| 5,843,091 A | 12/1998 | Holsinger et al. | |
| 5,882,347 A | 3/1999 | Mouris-Laan et al. | |
| 5,891,154 A | 4/1999 | Loeffler | |
| 5,906,619 A | 5/1999 | Olson et al. | |
| 5,954,764 A * | 9/1999 | Parodi | A61F 2/962 623/1.11 |
| 5,957,930 A | 9/1999 | Vrba | |
| 5,980,483 A | 11/1999 | Dimitri | |
| 6,017,577 A | 1/2000 | Hostettler et al. | |
| 6,019,778 A | 2/2000 | Wilson et al. | |
| 6,033,413 A | 3/2000 | Mikus et al. | |
| 6,059,813 A | 5/2000 | Vrba et al. | |
| 6,117,140 A | 9/2000 | Munsinger | |
| 6,120,522 A | 9/2000 | Vrba et al. | |
| 6,123,723 A | 9/2000 | Kónya et al. | |
| 6,139,510 A | 10/2000 | Palermo | |
| 6,139,524 A | 10/2000 | Killion | |
| 6,176,849 B1 | 1/2001 | Yang et al. | |
| 6,206,888 B1 * | 3/2001 | Bicek | A61F 2/95 606/108 |
| 6,221,467 B1 | 4/2001 | Nazarova et al. | |
| 6,238,410 B1 | 5/2001 | Vrba et al. | |
| 6,254,609 B1 | 7/2001 | Vrba et al. | |
| 6,273,895 B1 * | 8/2001 | Pinchuk | A61B 5/1076 606/108 |
| 6,287,329 B1 | 9/2001 | Duerig et al. | |
| 6,322,586 B1 | 11/2001 | Monroe et al. | |
| 6,330,884 B1 | 12/2001 | Kim | |
| 6,331,184 B1 | 12/2001 | Abrams | |
| 6,342,066 B1 | 1/2002 | Toro et al. | |
| 6,355,060 B1 | 3/2002 | Lenker et al. | |
| 6,375,676 B1 | 4/2002 | Cox | |
| 6,379,365 B1 | 4/2002 | Diaz | |
| 6,380,457 B1 | 4/2002 | Yurek et al. | |
| 6,391,050 B1 | 5/2002 | Broome | |
| 6,398,802 B1 | 6/2002 | Yee | |
| 6,425,898 B1 | 7/2002 | Wilson et al. | |
| 6,508,803 B1 | 1/2003 | Horikawa et al. | |
| 6,514,228 B1 | 2/2003 | Hamilton et al. | |
| 6,514,261 B1 | 2/2003 | Randall et al. | |
| 6,544,278 B1 | 4/2003 | Vrba et al. | |
| 6,576,006 B2 | 6/2003 | Limon et al. | |
| 6,589,251 B2 | 7/2003 | Yee et al. | |
| 6,602,226 B1 | 8/2003 | Smith et al. | |
| 6,613,014 B1 | 9/2003 | Chi | |
| 6,626,934 B2 | 9/2003 | Blaeser et al. | |
| 6,669,716 B1 * | 12/2003 | Gilson | A61F 2/95 606/108 |
| 6,709,667 B1 | 3/2004 | Lowe et al. | |
| 6,726,712 B1 | 4/2004 | Raeder-Devens et al. | |
| 6,726,714 B2 | 4/2004 | DiCaprio et al. | |
| 6,736,839 B2 | 5/2004 | Cummings | |
| 6,755,855 B2 | 6/2004 | Yurek et al. | |
| 6,773,446 B1 | 8/2004 | Dwyer et al. | |
| 6,776,791 B1 | 8/2004 | Stallings et al. | |
| 6,802,849 B2 | 10/2004 | Blaeser et al. | |
| 6,860,898 B2 | 3/2005 | Stack et al. | |
| 6,939,352 B2 * | 9/2005 | Buzzard | A61F 2/95 606/108 |
| 6,942,682 B2 | 9/2005 | Vrba et al. | |
| 6,951,675 B2 | 10/2005 | Chin et al. | |
| 7,001,423 B2 | 2/2006 | Euteneuer et al. | |
| 7,387,640 B2 | 6/2008 | Cummings | |
| 7,632,296 B2 | 12/2009 | Malewicz | |
| 7,740,652 B2 | 6/2010 | Gerdts et al. | |
| 7,766,952 B2 * | 8/2010 | Horan | A61F 2/95 623/1.11 |
| 8,128,676 B2 | 3/2012 | Cummings | |
| 8,152,818 B2 | 4/2012 | Gunderson | |
| 8,403,982 B2 | 3/2013 | Giannetti et al. | |
| 8,512,401 B2 * | 8/2013 | Murray, III | A61F 2/2436 623/1.11 |
| 8,562,673 B2 * | 10/2013 | Yeung | A61F 2/2412 623/1.12 |
| 2001/0034548 A1 | 10/2001 | Vrba et al. | |
| 2001/0034549 A1 | 10/2001 | Bartholf et al. | |
| 2001/0037141 A1 | 11/2001 | Yee et al. | |
| 2001/0051822 A1 * | 12/2001 | Stack | A61F 2/91 623/1.11 |
| 2002/0002396 A1 * | 1/2002 | Fulkerson | A61F 2/95 623/1.11 |
| 2002/0052641 A1 | 5/2002 | Monroe et al. | |
| 2002/0058951 A1 | 5/2002 | Fiedler | |
| 2002/0082550 A1 | 6/2002 | Hamilton et al. | |
| 2002/0095203 A1 | 7/2002 | Thompson et al. | |
| 2002/0103525 A1 | 8/2002 | Cummings | |
| 2002/0165523 A1 | 11/2002 | Chin et al. | |
| 2003/0074045 A1 * | 4/2003 | Buzzard | A61F 2/95 623/1.11 |
| 2003/0144671 A1 | 7/2003 | Brooks et al. | |
| 2003/0163156 A1 | 8/2003 | Hebert et al. | |
| 2004/0098083 A1 | 5/2004 | Tran et al. | |
| 2004/0148009 A1 | 7/2004 | Buzzard et al. | |
| 2004/0215317 A1 | 10/2004 | Cummings | |
| 2004/0267348 A1 | 12/2004 | Gunderson et al. | |
| 2005/0027305 A1 * | 2/2005 | Shiu | A61F 2/95 606/108 |
| 2005/0027345 A1 | 2/2005 | Horan et al. | |
| 2005/0080476 A1 | 4/2005 | Gunderson et al. | |
| 2005/0090887 A1 * | 4/2005 | Pryor | A61F 2/95 623/1.11 |
| 2005/0149159 A1 | 7/2005 | Andreas et al. | |
| 2005/0154439 A1 | 7/2005 | Gunderson | |
| 2005/0182473 A1 | 8/2005 | Eidenschink et al. | |
| 2005/0182475 A1 | 8/2005 | Jen et al. | |
| 2005/0192657 A1 | 9/2005 | Colen et al. | |
| 2005/0240254 A1 | 10/2005 | Austin | |
| 2005/0256562 A1 | 11/2005 | Clerc et al. | |
| 2005/0273151 A1 | 12/2005 | Fulkerson et al. | |
| 2006/0009833 A1 | 1/2006 | Chobotov et al. | |
| 2006/0030923 A1 | 2/2006 | Gunderson | |
| 2006/0041302 A1 | 2/2006 | Malewicz | |
| 2006/0074477 A1 | 4/2006 | Berthiaume et al. | |
| 2006/0190069 A1 | 8/2006 | Baker-Janis et al. | |
| 2006/0229697 A1 | 10/2006 | Gerdts et al. | |
| 2006/0292300 A1 | 12/2006 | Tan | |
| 2007/0135803 A1 | 6/2007 | Belson | |
| 2007/0142894 A1 | 6/2007 | Moore et al. | |
| 2007/0191865 A1 | 8/2007 | Pappas | |
| 2007/0208350 A1 | 9/2007 | Gunderson | |

(56) References Cited

U.S. PATENT DOCUMENTS

| | | | | |
|---|---|---|---|---|
| 2007/0233222 | A1* | 10/2007 | Roeder | A61F 2/95 623/1.11 |
| 2007/0255390 | A1* | 11/2007 | Ducke | A61F 2/95 623/1.11 |
| 2007/0282420 | A1 | 12/2007 | Gunderson | |
| 2008/0188920 | A1 | 8/2008 | Moberg et al. | |
| 2008/0208320 | A1 | 8/2008 | Tan-Malecki et al. | |
| 2008/0255651 | A1* | 10/2008 | Dwork | A61F 2/95 623/1.11 |
| 2008/0294267 | A1 | 11/2008 | Chanduszko | |
| 2009/0024133 | A1 | 1/2009 | Keady et al. | |
| 2009/0030495 | A1* | 1/2009 | Koch | A61F 2/95 623/1.11 |
| 2009/0036967 | A1 | 2/2009 | Cummings | |
| 2009/0157162 | A1 | 6/2009 | Chow et al. | |
| 2009/0192584 | A1 | 7/2009 | Gerdts et al. | |
| 2009/0254165 | A1* | 10/2009 | Tabor | A61F 2/2412 623/1.11 |
| 2010/0234933 | A1* | 9/2010 | Punga | A61F 2/95 623/1.12 |
| 2010/0256727 | A1 | 10/2010 | Gerdts et al. | |
| 2011/0257718 | A1* | 10/2011 | Argentine | A61F 2/966 623/1.11 |
| 2011/0257719 | A1* | 10/2011 | Argentine | A61F 2/95 623/1.11 |
| 2011/0270371 | A1* | 11/2011 | Argentine | A61F 2/95 623/1.11 |
| 2011/0282425 | A1* | 11/2011 | Dwork | A61F 2/95 623/1.11 |
| 2012/0221091 | A1* | 8/2012 | Hartly | A61F 2/95 623/1.11 |
| 2013/0103130 | A1* | 4/2013 | Lubinski | A61F 2/966 623/1.11 |
| 2013/0131774 | A1* | 5/2013 | Nabulsi | A61F 2/95 623/1.11 |
| 2013/0166012 | A1* | 6/2013 | Bowe | A61F 2/95 623/1.11 |
| 2014/0088686 | A1* | 3/2014 | Centola | A61F 2/2412 623/1.12 |
| 2015/0305902 | A1* | 10/2015 | Argentine | A61F 2/966 623/1.12 |

FOREIGN PATENT DOCUMENTS

| | | |
|---|---|---|
| EP | 0775470 A1 | 5/1997 |
| EP | 0633756 B1 | 2/1998 |
| EP | 0820259 B1 | 2/2003 |
| EP | 1385450 B1 | 3/2007 |
| WO | 9717899 A1 | 5/1997 |
| WO | 9949808 A1 | 10/1999 |
| WO | 0018330 A1 | 4/2000 |
| WO | 0023139 A1 | 4/2000 |
| WO | 0027309 A1 | 5/2000 |
| WO | 0067828 A1 | 11/2000 |
| WO | 0071059 A1 | 11/2000 |
| WO | 0176676 A2 | 10/2001 |
| WO | 2002056953 A2 | 7/2002 |
| WO | 2004098692 A1 | 11/2004 |
| WO | 2005020856 A2 | 3/2005 |
| WO | 2005107644 A1 | 11/2005 |
| WO | 2005112824 A1 | 12/2005 |
| WO | 2006036472 A1 | 4/2006 |
| WO | 2007084370 A1 | 7/2007 |

* cited by examiner

MEDICAL DEVICE DELIVERY SYSTEM WITH FORCE REDUCTION MEMBER

CROSS-REFERENCE TO RELATED APPLICATIONS

This application claims priority under 35 U.S.C. § 119(e) to U.S. Provisional Application No. 62/104,434, filed Jan. 16, 2015, the entire disclosure of which is herein incorporated by reference.

TECHNICAL FIELD

The present disclosure pertains to medical devices, and methods for manufacturing medical devices. More particularly, the present disclosure pertains to medical device delivery systems with a force reduction member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods.

SUMMARY

This disclosure provides design, material, manufacturing method, and use alternatives for medical devices. An example medical device is disclosed. The medical device comprises:
a catheter shaft including:
an inner member having a distal region, and
a deployment sheath disposed about the inner member;
a stent disposed along the distal region of the inner member;
a handle coupled to the catheter shaft;
an actuation mechanism coupled to the handle for proximally retracting the deployment sheath;
wherein the actuation mechanism is designed to shift relative to the handle from a pre-deployment position, along an early deployment region, and along a full deployment region; and
a force reduction member for applying a force to the actuation mechanism while the actuation mechanism is disposed along the early deployment region.

Alternatively or additionally to any of the embodiments above, the stent includes a self-expanding stent.

Alternatively or additionally to any of the embodiments above, the actuation mechanism includes a control button.

Alternatively or additionally to any of the embodiments above, the control button is rotatable relative to the handle.

Alternatively or additionally to any of the embodiments above, shifting the actuation mechanism from the pre-deployment position to the early deployment region includes rotating the control button.

Alternatively or additionally to any of the embodiments above, the control button is axially slidable along the handle.

Alternatively or additionally to any of the embodiments above, the control button is axially slidable along the full deployment region.

Alternatively or additionally to any of the embodiments above, the force reduction member includes a spring.

Alternatively or additionally to any of the embodiments above, the handle has a slot formed therein, the slot having an angled section and an axial section.

Alternatively or additionally to any of the embodiments above, the actuation mechanism is designed to move along the slot.

Alternatively or additionally to any of the embodiments above, when the actuation mechanism is shifted to the early deployment region the actuation mechanism is positioned along the angled section of the slot.

Alternatively or additionally to any of the embodiments above, when the actuation mechanism is shifted to the full deployment region the actuation mechanism is positioned along the axial section of the slot.

A medical device delivery system is disclosed. The medical device delivery system comprises:
an inner member having a distal region;
a stent disposed along the distal region;
a deployment sheath disposed about the stent;
a handle coupled to the deployment sheath;
a control button movably disposed along the handle for proximally retracting the deployment sheath;
wherein the control button is designed to shift between a pre-deployment position and a full deployment position; and
a force reduction member for reducing the amount of force required for shifting the control button from the pre-deployment position to the full deployment position.

Alternatively or additionally to any of the embodiments above, shifting the control button from the pre-deployment position to the full deployment position includes rotating the control button.

Alternatively or additionally to any of the embodiments above, the force reduction member includes a spring.

Alternatively or additionally to any of the embodiments above, the handle has a slot formed therein, the slot having an angled section and an axial section.

Alternatively or additionally to any of the embodiments above, shifting the control button from the pre-deployment position to the full deployment position includes shifting the control button along the angled section of the slot.

Alternatively or additionally to any of the embodiments above, when the control button is shifted to the full deployment position, the control button is axially slidable along the axial section of the slot.

Alternatively or additionally to any of the embodiments above, the deployment sheath includes a pull wire, and wherein the pull wire is secured to the control button.

A method for delivering a self-expanding stent is disclosed. The method comprises:
advancing a stent delivery system through a body lumen to a position adjacent to a target region;
wherein the stent delivery system includes:
an inner member having a distal region,
a stent disposed along the distal region,
a deployment sheath disposed about the stent,
a handle coupled to the deployment sheath,
a control button movably disposed along the handle for proximally retracting the deployment sheath,
wherein the control button is designed to shift between a pre-deployment position and a full deployment position, and
a force reduction member for reducing the amount of force required for shifting the control button from the pre-deployment position to the full deployment position;
shifting the control button from the pre-deployment position to the full deployment position; and
proximally sliding the control button along the handle.

BRIEF DESCRIPTION OF THE DRAWINGS

The disclosure may be more completely understood in consideration of the following detailed description in connection with the accompanying drawings, in which.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

Figure 1:
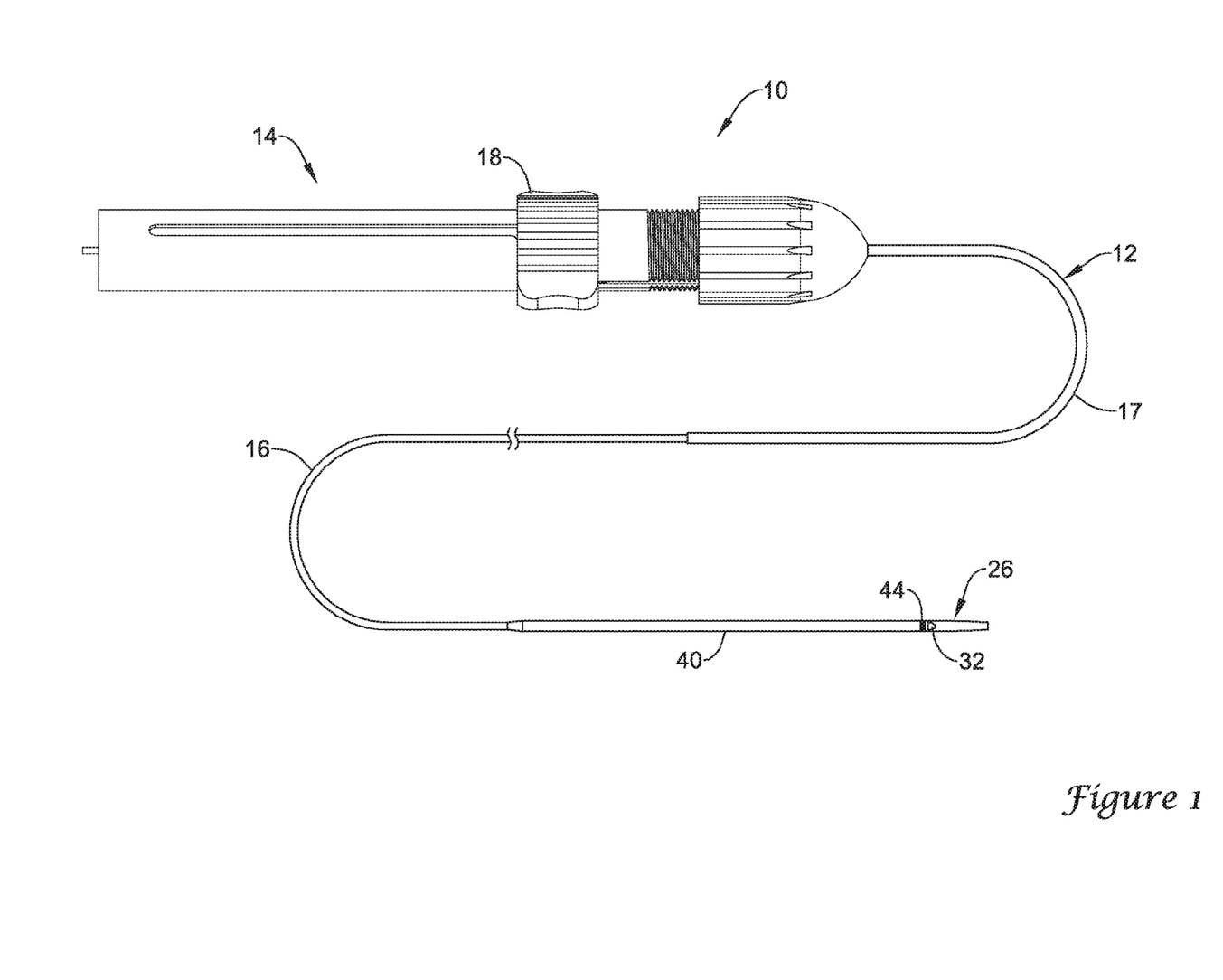
FIG. 1 is a side view of an example stent delivery system.

FIG. 1 illustrates an example stent delivery system 10. System 10 may include a catheter shaft 12 and a handle 14 coupled to shaft 12. In general, system 10 may be used to deliver a suitable stent, graft, endoprosthesis or the like to an area of interest within a body lumen of a patient. The body lumen may be a blood vessel located near the heart (e.g., within or near a cardiac vessel), within a peripheral vessel, within a neurological vessel, along a non-vascular region such as along the biliary and/or pancreatic tract, or at any other suitable location. Deployment of the stent may include the proximal retraction of a deployment sheath 16, which overlies the stent. In some instances, catheter shaft 12 may include an outer tube or member 17. Outer tube 17 may have a distal end that is disposed proximally of the distal end of deployment sheath 16.

Retraction of sheath 16 may include the actuation or use of an actuation member 18 generally disposed at handle 14. In the example illustrated in FIG. 1, actuation member 18 is a control button that can be slid along handle 14 in order to accomplish proximal retraction of deployment sheath 16. Numerous other actuation members are contemplated including a thumb wheel. A number of other structures and features of system 10 can be seen in FIG. 1 and are labeled with reference numbers. Additional discussion of these structures can be found below.

Figure 2:
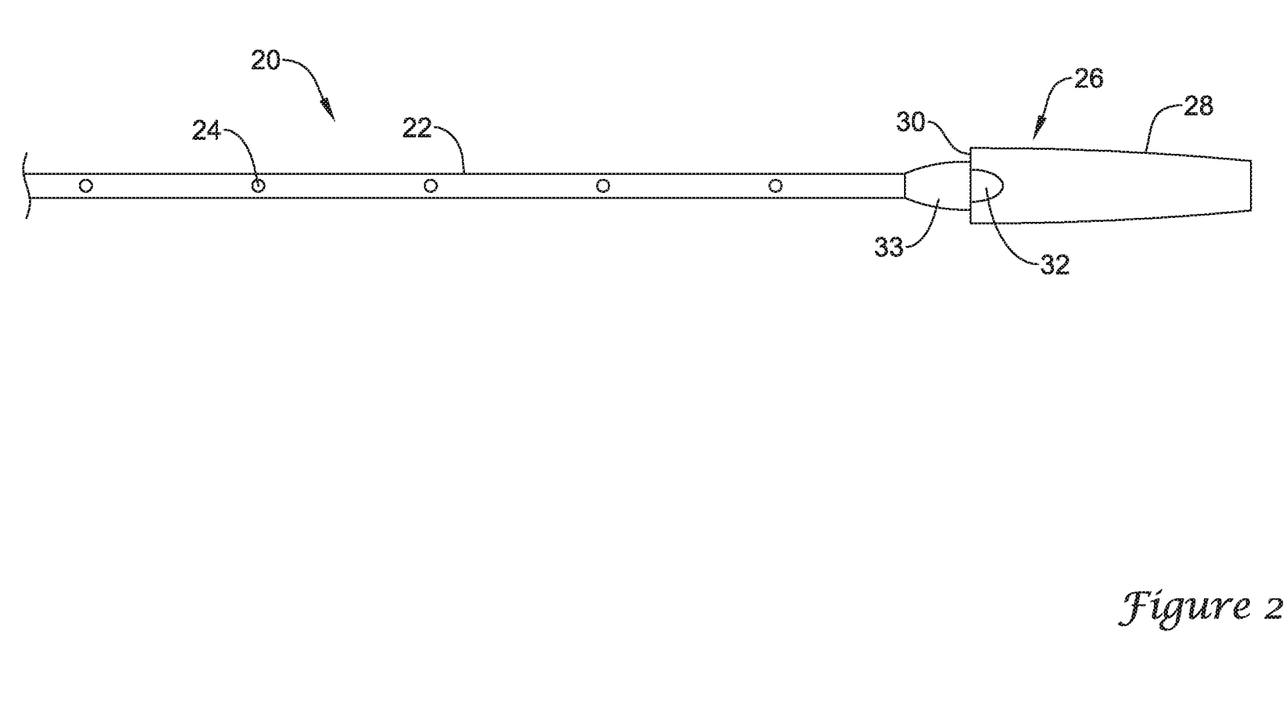
FIG. 2 is a side view of a portion of an example stent delivery system.
Figure 3:
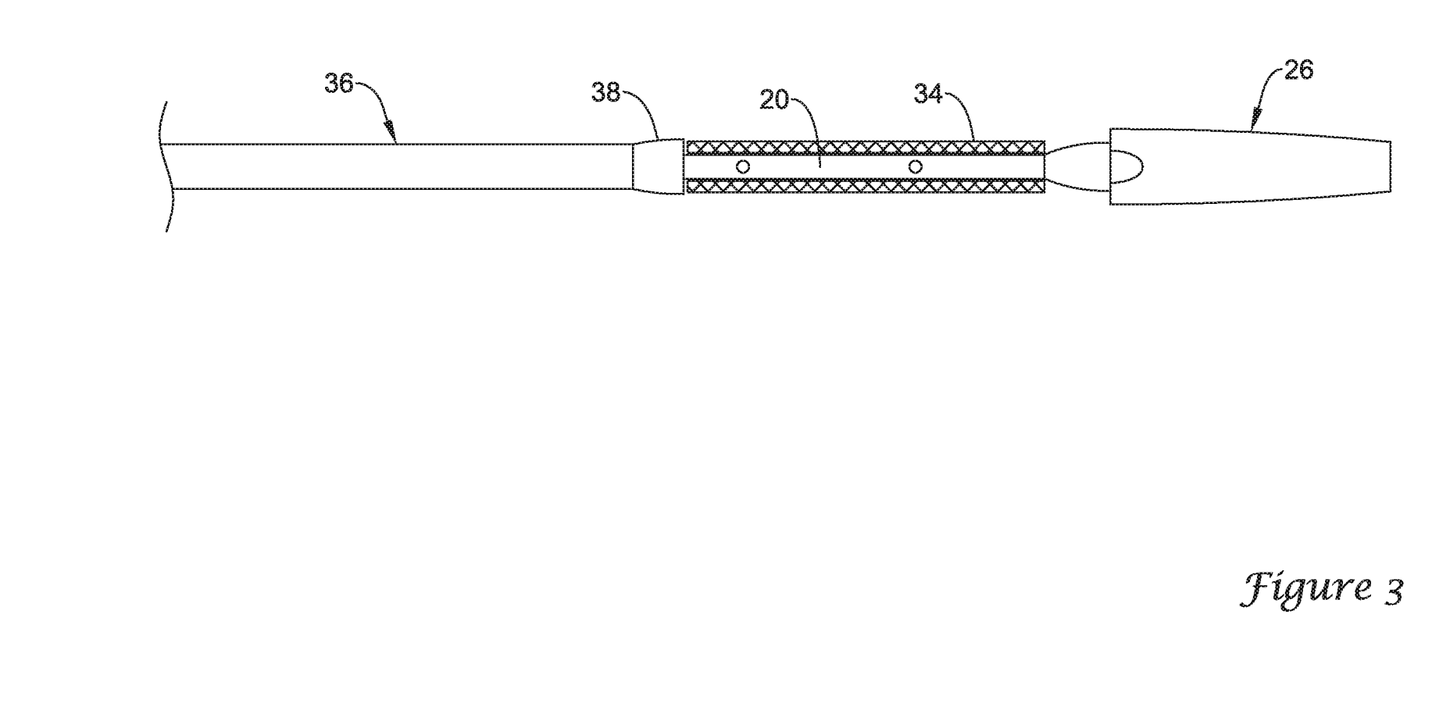
FIG. 3 is a side view of a portion of an example stent delivery system.
Figure 4:
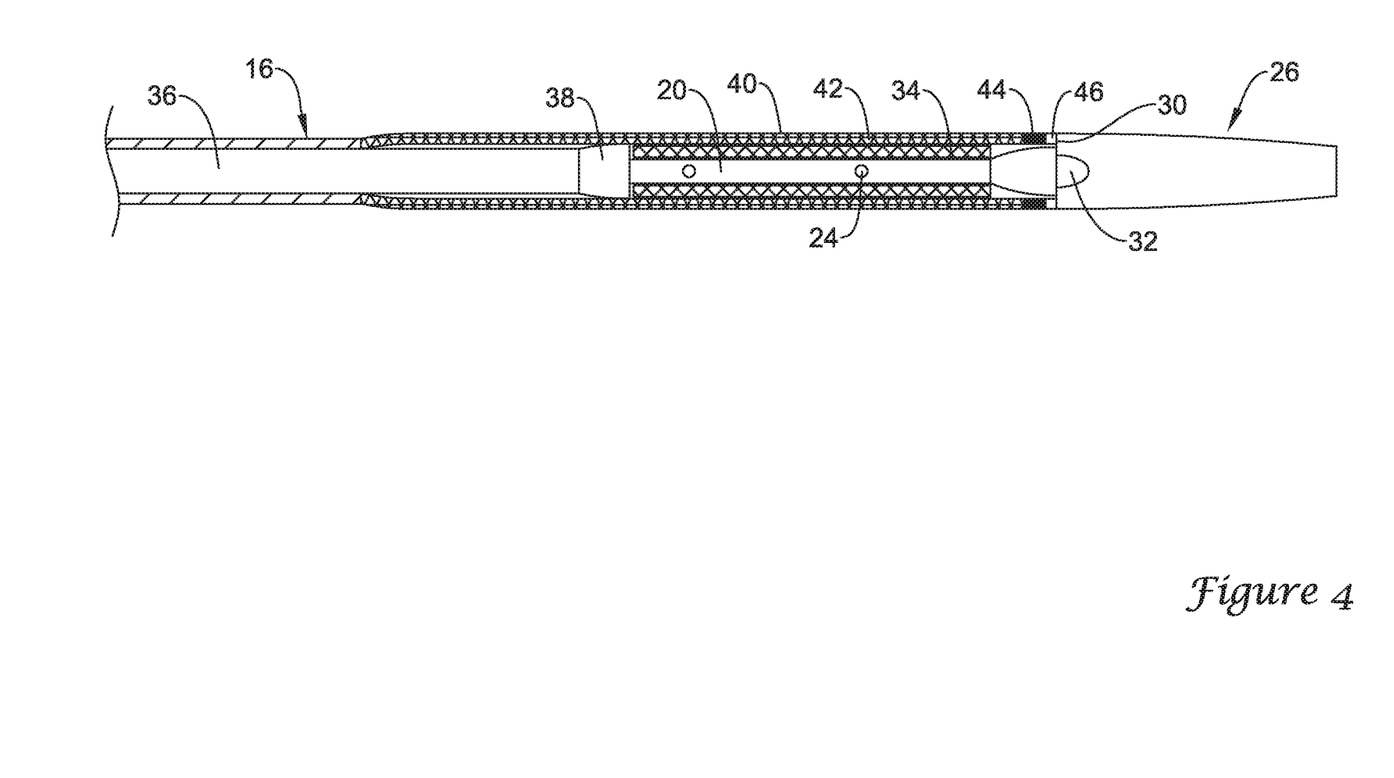
FIG. 4 is a partially cross-sectional side view of a portion of an example stent delivery system.

FIGS. 2-4 illustrate at least some of the structural components that may be included as a part of system 10. For example, system 10 may include an inner shaft or member 20 as illustrated in FIG. 2. In at least some embodiments, inner member 20 may be a tubular structure and, thus, may include a lumen (not shown). The lumen may be a guidewire lumen that extends along at least a portion of the length of inner member 20. Accordingly, system 10 may be advanced over a guidewire to the desired target location in the vasculature. In addition, or in alternative embodiments, the lumen may be a perfusion/aspiration lumen that allows portions, components, or all of system 10 to be flushed, perfused, aspirated, or the like.

Inner member 20 may include a stent receiving region 22 about which a stent (not shown, can be seen in FIGS. 3-4) may be disposed. The length and/or configuration of stent receiving region 22 may vary. For example, stent receiving region 22 may have a length sufficient for the stent to be disposed thereon. It can be appreciated that as the length of the stent utilized for system 10 increases, the length of stent receiving region 22 also increases.

Along or otherwise disposed adjacent stent receiving region 22 may be one or more perfusion ports 24. Ports 24 may extend through the wall of inner member 20 such that fluid may be infused through the lumen of inner member 20 and may be flushed through ports 24. This may be desirable for a number of reasons. For example, ports 24 may allow a clinician to evacuate air bubbles that may be trapped adjacent the stent by perfusing fluid through ports 24. In addition, ports 24 may be used to aspirate fluid that may be disposed along inner member 20. Ports 24 may also aid in sterilization and/or other preparatory processing steps that may be involved in preparing system 10 for sale.

A tip 26 may be attached to or otherwise disposed at the distal end of inner member 20. Tip 26 may generally have a rounded or smooth shape that provides a generally atraumatic distal end to system 10. For example, tip 26 may have a smooth tapered distal portion 28 that gently tapers. Tip may also include a proximal ridge 30 that is configured so that sheath 16 can abut therewith. Tip 26 may also include a tapered proximal portion 33. Numerous other shapes and/or configurations may be implemented for tip 26.

Tip 26 may also include one or more cutouts or flats 32 formed therein. For the purposes of this disclosure, flats 32 are understood to be cutouts or flattened portions of tip 26 where the outer dimension or profile of tip 26 is reduced. The name "flats" comes from the fact that these regions may have a somewhat "flat" appearance when compared to the remainder of tip 26, which generally may have a rounded profile. The shape, however, of flats 32 is not meant to be limited to being flat or planar as numerous shapes are contemplated.

Flats 32 may allow for a gap or space to be defined between inner member 20 and deployment sheath 16 when sheath 16 abuts proximal ridge 30 of tip 26. This gap may allow for fluid, for example perfusion fluid passed through ports 24, to flow out from sheath 16. Thus, flats 32 may be used in conjunction with ports 24 to allow portions or all of system 10 to be flushed or otherwise evacuated of air bubbles.

FIG. 3 illustrates inner member 20 with some additional structure of system 10. In this figure, a stent 34 is disposed about inner member 20 (e.g., about stent receiving region 22 of inner member 20). In some embodiments, stent 34 is a self-expanding stent. Accordingly, stent 34 may be biased to outwardly expand. Because of this, stent 34 may not be "loaded onto" inner member 20 in a strict sense but rather may be thought of as being disposed about or surrounding inner member 20. Stent 34 may then be restrained within deployment sheath 16. In alternative embodiments, however, stent 34 may be directly loaded onto inner member 20 via crimping or any other suitable mechanical holding mechanism.

An intermediate tube 36 may also be disposed over inner member 20. In at least some embodiments, intermediate tube 36 may extend from a position adjacent to the proximal end of inner member 20 to a position proximal of the distal end of inner member 20. Intermediate tube 36 may include a bumper 38. In practice, bumper 38 may function by preventing any unwanted proximal movement of stent 34 during navigation and/or deployment of stent 34.

Bumper 38 may have any suitable form. In some embodiments, bumper 38 may be defined by a relatively short tube or sleeve that is disposed about intermediate tube 36. The material utilized for the sleeve may be the same or different from that of intermediate tube 36. Intermediate tube 36 may have a tapered or otherwise smooth transition in outer diameter adjacent bumper 38. For example, polymeric material may be disposed or reflowed adjacent bumper 38 (which may include disposing the polymeric material about a portion or all of bumper 38) so as to define a gentle transition in outer diameter at bumper 38. Other configurations are contemplated and may be utilized in alternative embodiments.

FIG. 4 illustrates additional structure of system 10. Here deployment sheath 16 can be seen disposed over inner member 20, intermediate tube 36, and stent 34. It can be appreciated that sheath 16 is configured to shift between a first position, for example as shown in FIG. 4, where sheath 16 overlies stent 34 and a second position where sheath 16 is proximally retracted to a position substantially proximal of stent 34. In general, the first position may be utilized during navigation of system 10 to the appropriate location within a body lumen and the second position may be used to deploy stent 34.

Sheath 16 may include a flared portion 40 where the outer diameter of sheath 16 is increased. In flared portion 40, the thickness of the tubular wall of sheath 16 may or may not be increased. Flared portion 40 may be desirable for a number of reasons. For example, flared portion 40 may allow sheath 16 to have an adequate inner dimension that is suitable so that sheath 16 may be disposed about stent 34 and bumper 38.

In at least some embodiments, sheath 16 may include a reinforcing member 42 embedded or otherwise included therewith. Reinforcing member 42 may have any number of a variety of different configurations. For example, reinforcing member 42 may include a braid, coil, mesh, combinations thereof, or the like, or any other suitable configuration. In some embodiments, reinforcing member 42 may extend along the entire length of sheath 16. In other embodiments, reinforcing member 42 may extend along one or more portions of the length of sheath 16. For example, reinforcing member 42 may extend along flared portion 40.

Sheath 16 may also include a radiopaque marker or band 44. In general, marker band 44 may be disposed adjacent to the distal end 46 of sheath 16. One or more additional marker bands 44 may be disposed along other portions of sheath 16 or other portions of system 10. Marker band 44 may allow the distal end 46 of sheath 16 to be fluoroscopically visualized during advancement of system 10 and/or deployment of stent 34.

FIG. 4 also illustrates the distal end 46 of sheath 16 abutting proximal ridge 30. In this configuration, stent 34 can be flushed (e.g., to remove air bubbles) by infusing fluid through inner member 20 and through ports 24. Because of flats 32, fluid may be allowed to be flushed out of sheath 16 by passing through the gaps formed between inner member 20 and sheath 16 at flats 32.

As indicated herein, stent 34 may be a self-expanding stent. The radially outward expansion force that stent 34 may exert onto deployment sheath 16 may make it somewhat difficult to initiate proximal retraction of deployment sheath 16. In other words, the amount of force required to initiate proximal retraction of deployment sheath 16 may be relatively high and, in some instances, may be high enough to cause a clinician to unintentionally shift the position of system 10 during deployment of stent 34, which may impact delivery precision. Because of this, system 10 includes structural features that allow deployment sheath 16 to be more easily retracted (e.g., with a lower initial retraction force).

Figure 5:
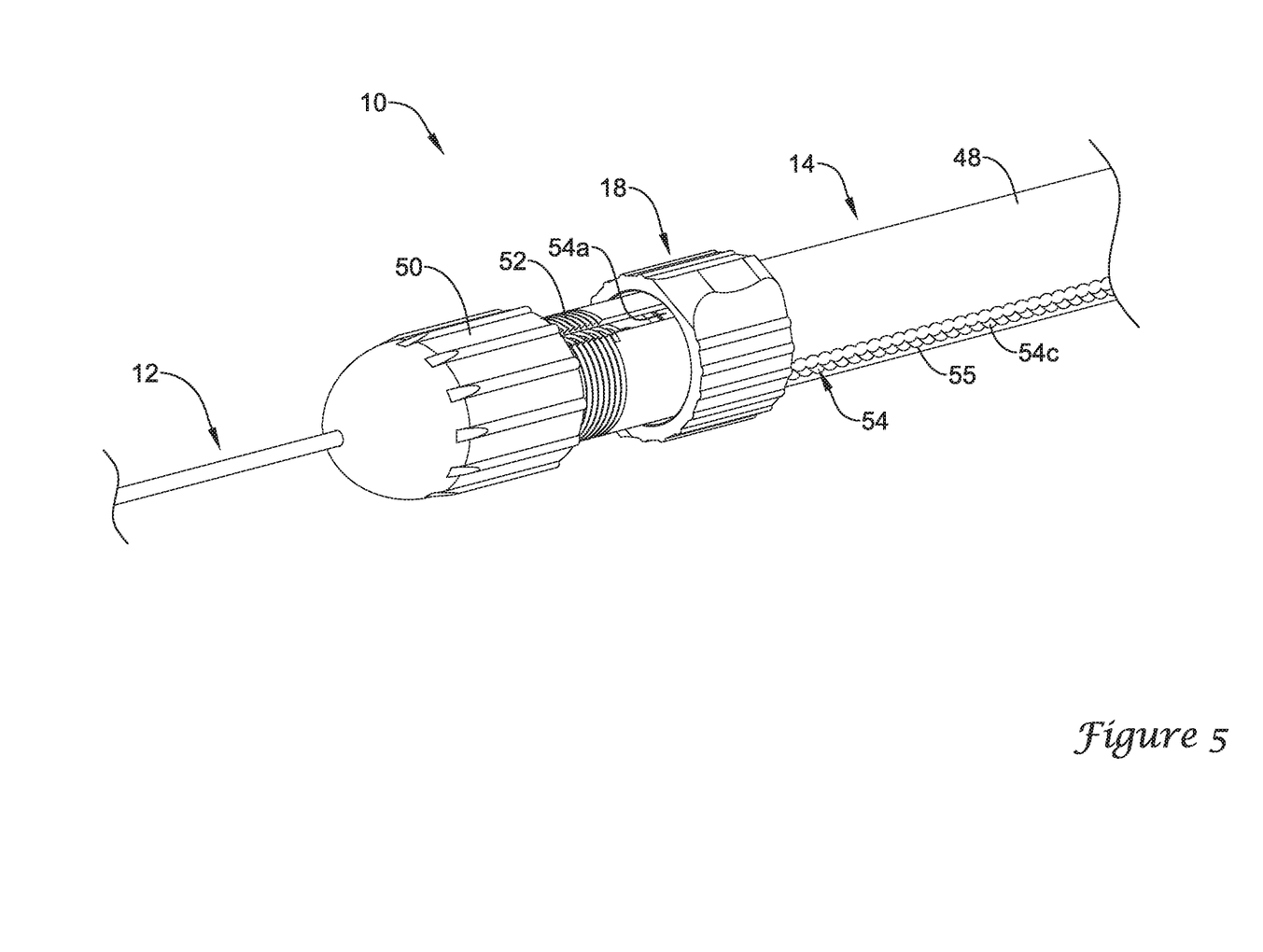
FIG. 5 is a perspective view of a portion of an example stent delivery system.

FIG. 5 illustrates a portion of handle 14 of system 10. Handle 14, in general, is designed so that proximal retraction of deployment sheath 16, particularly the initial proximal retraction of deployment sheath 16, can be accomplished a reduced amount of force. In at least some instances, handle 14 has a mechanical "force reduction" or assist device that aids in reducing the (e.g., "early" or initial) deployment forces. The force reduction member may apply a force (e.g., a linear force in the distal direction) onto actuation member 18 so that actuation member 18 can overcome resistance that may be present due to, for example, radially forces exerted on deployment sheath 16 by stent 34.

Figure 7:
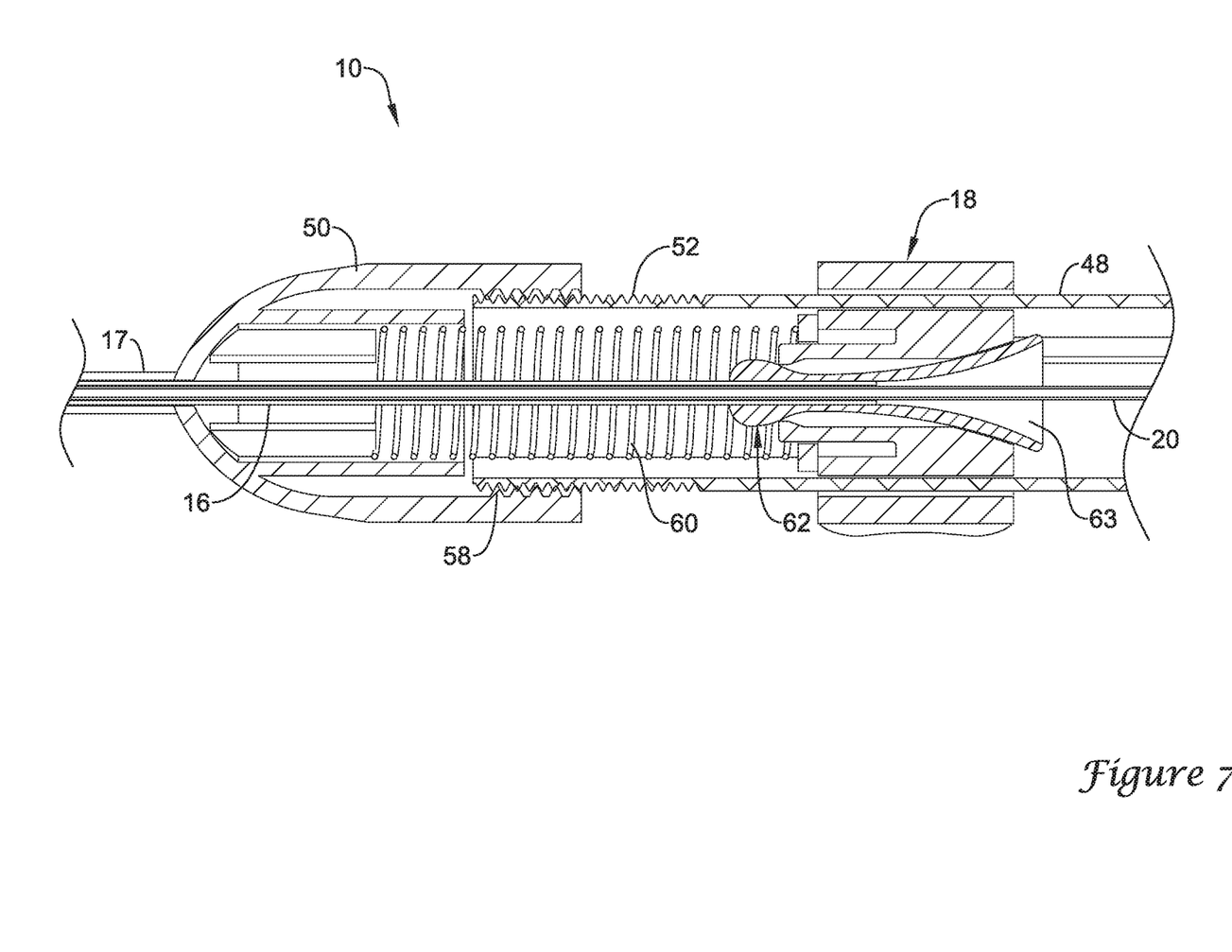
FIG. 7 is a partially cross-sectional side view of a portion of an example stent delivery system.
Figure 8:
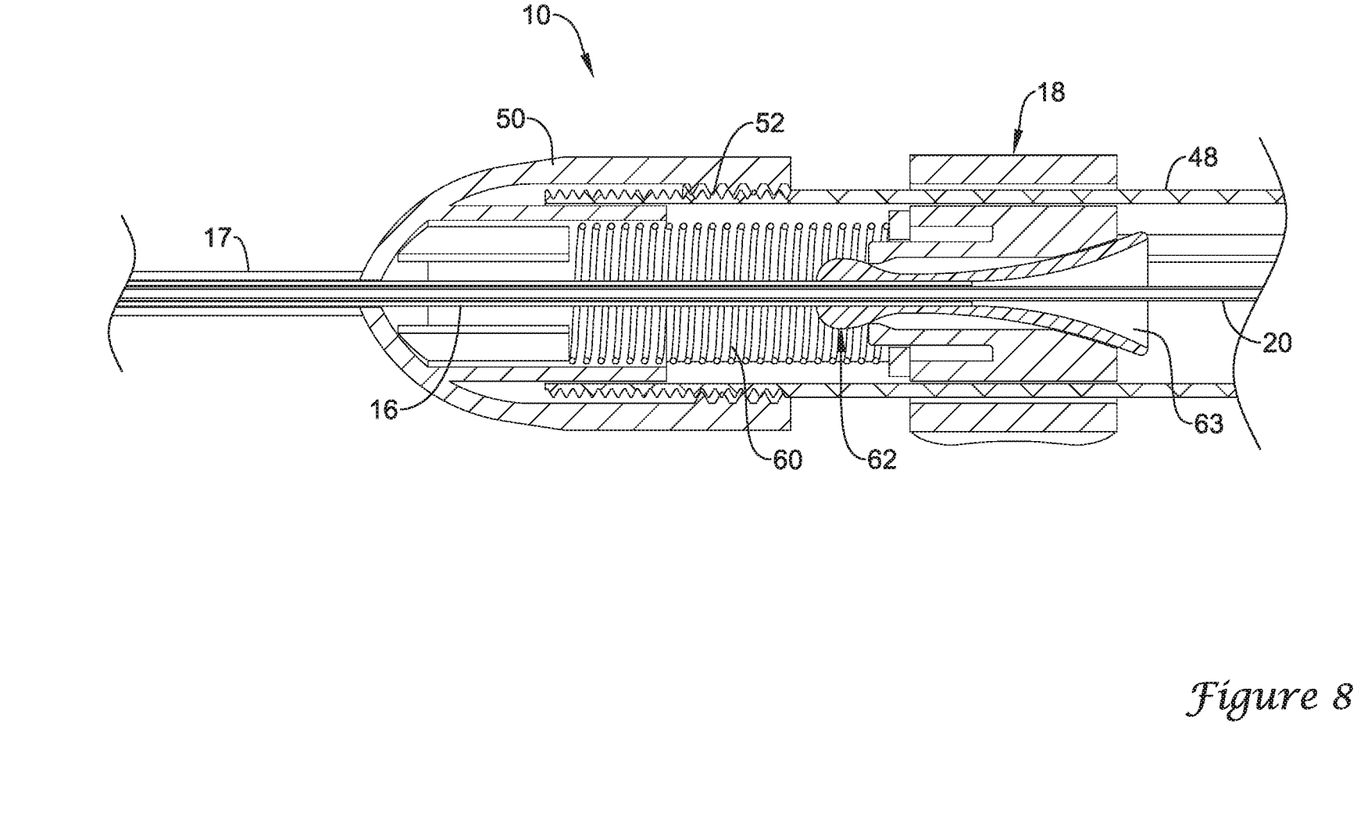
FIG. 8 is a partially cross-sectional side view of a portion of an example stent delivery system.

Handle 14 includes a handle body 48. A cap or nut 50 is threadably connected to a threaded region 52 of handle body 48. Rotating cap 50 may result in compression of a force reducing member 60, as shown in FIGS. 7-8, for example. Force reducing member 60 may apply a force upon actuation member 18 to help initiate proximal retraction of deployment sheath 16. In some instances, cap 50 may be disposed in a loosely threaded configuration prior to use of system 10 (e.g., including during packaging and shipping). This may allow force reducing member 60 to be disposed in a relaxed state so that forces present in system 10 can be kept to a minimum prior to use. When a clinician is prepared to use system 10, cap 50 can be rotated to compress force reducing member 60. This may cause force reducing member 60 to apply a force onto actuation member 18. It can be appreciated that the level of force applied onto actuation member 18 can be tailored to the particular needs of an intervention via greater or lesser amounts of cap 50 rotation. In other words, if a greater amount of force reduction is desired, cap 50 can be rotated to a greater extent in order to further compress force reducing member 60. In some instances, cap 50 may be designed to include a torque control mechanism so that cap 50 declutches and turns freely upon reaching a predetermined "maximum" torque (e.g., force reducing member is loaded to a pre-determined maximum allowable force to assist deployment or is otherwise fully compressed).

Figure 6:
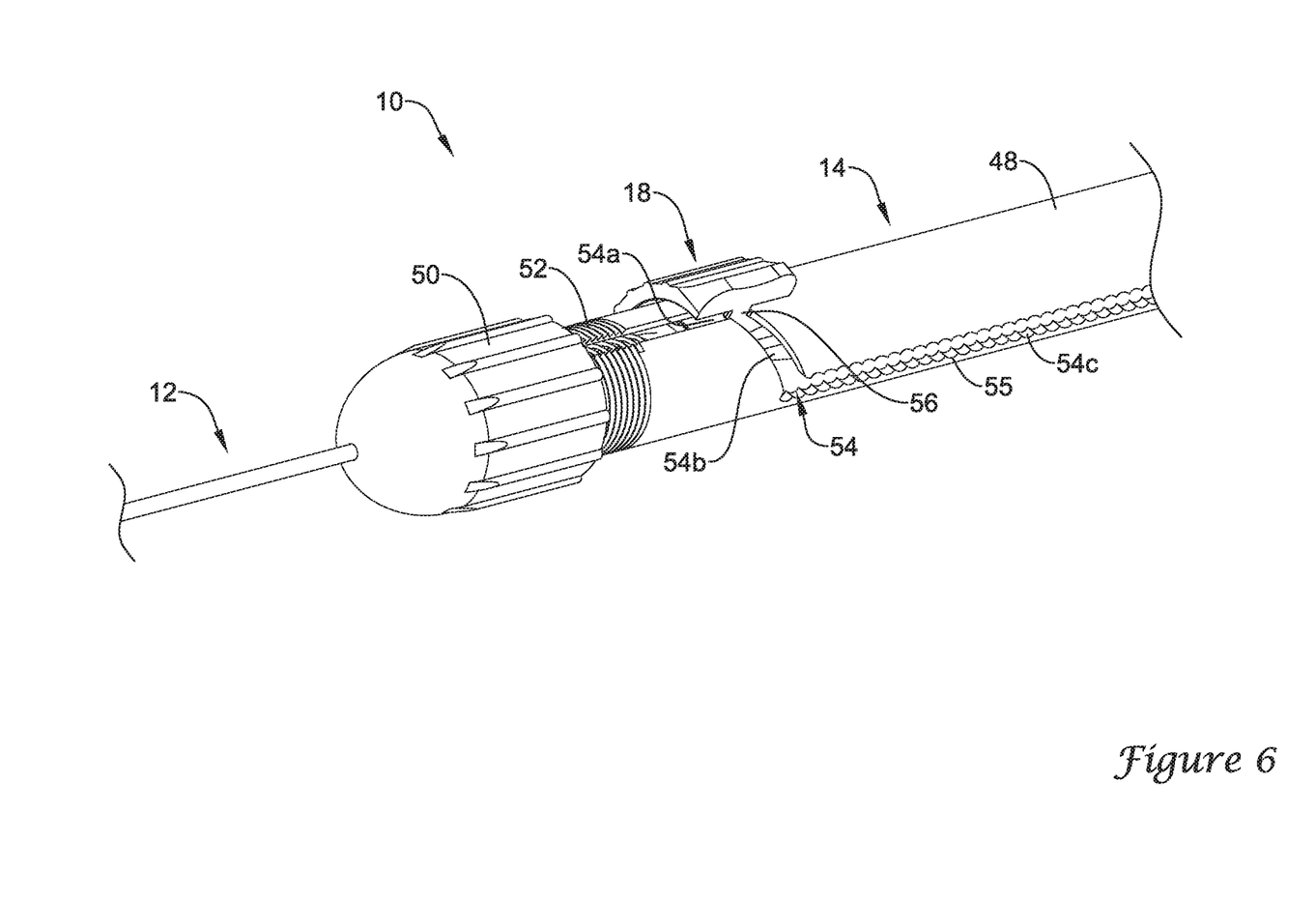
FIG. 6 is a partially cut away perspective view of a portion of an example stent delivery system.

Handle body 48 has a slot or channel 54 formed therein. Slot 54 includes a first or "pre-deployment" section/position 54a, a second or "early deployment" section/region 54b (e.g., as shown in FIG. 6 where a portion of actuation member 18 is cut away), and a third or "full deployment" section/region 54c. In at least some instances, early deployment region 54b is oriented at an angle (e.g., oriented at an angle relative to the longitudinal axis of handle body 48) and/or takes the form of a cam slot. This may allow for deployment of sheath 16 in a gradual manner (e.g., by sliding/rotating actuation member 18 along region 54b). Full deployment region 54c may extend axially along handle 14. Portions of slot 54 may include a structure that helps to slow or reduce motion of actuation member 18. For example, full deployment region 54c of slot 54 (and/or other portions of slot 54) may include a series of notches or projections 55. Notches 55 may help reduce the slow the movement or otherwise prevent unwanted movement of actuation member 18 if, for example, force reducing member 60 continues to apply any forces to actuation member 18 after shifting actuation member 18 from early deployment region 54b to full deployment region 54c.

The movement of actuation member 18 along region 54b and/or slot 54c may also be designed to allow for reconstrainment and/or repositioning of stent 34. For example, actuation member 18 can move forward (e.g., distally) and backward (e.g., proximally) along slot 54c and notches 55 allow a clinician to stop at a controlled position, reconstrain stent 34 (e.g., by distally moving actuation member 18), reposition stent 34 to a desired location by moving system 10 relative to the target, and then slide actuation member 18 an additional time to deploy stent 34.

Actuation member 18 is designed to move along slot 54. As shown in FIG. 6, actuation member 18 may be positioned at pre-deployment position 54a. When doing so, a radially-inward extending projection 56 of actuation member 18 may extend within slot 54. Initial or early deployment of deployment sheath 16 may occur by rotating actuation member 18 into and along early deployment region 54b. This may include shifting/rotating projection 56 of actuation member 18 from pre-deployment position 54a to/along early deployment region 54b. Force reducing member 60, which may be in a compressed state, can apply a force onto actuation member 18 during this rotation. Because of this, the force required to rotate actuation member 18 and shift actuation member 18 from pre-deployment position 54a to early deployment region 54b may be reduced. Shifting actuation member 18 from pre-deployment position 54a to early deployment region 54b may initiate retraction of deployment sheath 16. After deployment sheath 16 is initially deployed, lower deployment forces may be suitable to finish the deployment of stent 34. The remaining proximal retraction of deployment sheath 16 may occur by sliding actuation member 18 along full deployment region 54c until stent 34 is deployed.

FIG. 7 is a cross-sectional view of system 10. Here it can be seen that force reducing member 60 may take the form of a spring. Spring 60 may engage actuation member 18 so that spring 60 may exert a force onto actuation member 18 (e.g., in the proximal direction). Also shown in FIG. 7 is that actuation member 18 may include a guidewire port member 62. In at least some instances, guidewire port member 62 may be secured to actuation member 18. Guidewire port member 62 may define or otherwise includes a guidewire port 63. Port 63 may extend to the exterior of handle body 48 so that a guidewire may be disposed therein. Alternatively, a guidewire port may be disposed at another position along handle 14 such as at the proximal end of handle 14. Deployment sheath 16 may be secured to guidewire port member 62 (and/or actuation member 18). In some instances, deployment sheath 16 may terminate distally of handle 14 and a pull wire (not shown) may be attached to the proximal end of deployment sheath 16 and extend to guidewire port member 62 (and/or actuation member 18). Other configurations are contemplated.

While force reducing member 60 may be a spring in some instances, other force reducing members are contemplated. For example, force reducing member 60 may take the form of a linear actuator (and/or a spring and linear actuator). Such a force reducing member 60 may generate a linear force electrically, pneumatically, hydraulically, etc.

Cap 50 may have an internal thread 58 that is designed to engage with threaded region 52. Thus, as disclosed herein cap 50 may be disposed in a loosely threaded configuration (e.g., as shown in FIG. 7). This configuration may be desirable prior to use and during packaging/shipping. When desired for use, cap 50 can be rotated to compress force reducing member 60 as shown in FIG. 8 and, thus, pre-load force reducing member 60.

While, handle 14 is described as an integral component of system 10, this is not intended to be limiting. For example, handle 14 (including force reducing member 60) may be a separate device that can be added onto and used with another system (e.g., another stent delivery system). In other words, handle 14 may be an "add-on" that can be manufactured and sold separately from a system and then added to the system to provide the desirable features of handle 14 to the system.

The materials that can be used for the various components of system 10 (and/or other systems disclosed herein) and the various tubular members disclosed herein may include those commonly associated with medical devices. For simplicity purposes, the following discussion makes reference to catheter shaft 12 and other components of system 10. However, this is not intended to limit the devices and methods described herein, as the discussion may be applied to other similar tubular members and/or components of tubular members or devices disclosed herein.

Catheter shaft 12 and/or other components of system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10 to achieve the same result.

In some embodiments, a degree of Magnetic Resonance Imaging (MRI) compatibility is imparted into system 10. For example, catheter shaft 12, or portions thereof, may be made of a material that does not substantially distort the image and create substantial artifacts (e.g., gaps in the image). Certain ferromagnetic materials, for example, may not be suitable because they may create artifacts in an MRI image. Catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

What is claimed is:
1. A medical device, comprising:

a catheter shaft including:
   an inner member having a distal region, and
   a deployment sheath disposed about the inner member;
a stent disposed along the distal region of the inner member;
a handle coupled to the catheter shaft;
an actuation mechanism coupled to the handle for proximally retracting the deployment sheath;
wherein the actuation mechanism is designed to shift axially along the handle from a pre-deployment position, along an early deployment region, and along a full deployment region; and
a force reduction member, the force reduction member being designed to apply a force to the actuation mechanism while the actuation mechanism is disposed along the early deployment region;
wherein the handle has a slot formed therein, the slot having an angled section and an axial section;
wherein the actuation mechanism is designed to move along the slot; and
wherein when the actuation mechanism is shifted to the full deployment region the actuation mechanism is positioned along the axial section of the slot.

2. The medical device of claim 1, wherein the stent includes a self-expanding stent.

3. The medical device of claim 1, wherein the actuation mechanism includes a control button.

4. The medical device of claim 3, wherein the control button is rotatable relative to the handle.

5. The medical device of claim 4, wherein shifting the actuation mechanism from the pre-deployment position to the early deployment region includes rotating the control button.

6. The medical device of claim 5, wherein the control button is axially slidable along the handle.

7. The medical device of claim 6, wherein the control button is axially slidable along the full deployment region.

8. The medical device of claim 1, wherein the force reduction member includes a spring.

9. The medical device of claim 1, wherein when the actuation mechanism is shifted to the early deployment region the actuation mechanism is positioned along the angled section of the slot.

10. A medical device delivery system, comprising:
an inner member having a distal region;
a stent disposed along the distal region;
a deployment sheath disposed about the stent;
a handle coupled to the deployment sheath;
wherein the deployment sheath includes a pull wire;
a control button secured to the pull wire is movably disposed along the handle for proximally retracting the deployment sheath;
wherein the control button is designed to shift between a pre-deployment position and a full deployment position; and
a force reduction member for reducing the amount of force required for shifting the control button from the pre-deployment position to the full deployment position.

11. The system of claim 10, wherein shifting the control button from the pre-deployment position to the full deployment position includes rotating the control button.

12. The system of claim 10, wherein the force reduction member includes a spring.

13. The system of claim 10, wherein the handle has a slot formed therein, the slot having an angled section and an axial section.

14. The system of claim 13, wherein shifting the control button from the pre-deployment position to the full deployment position includes shifting the control button along the angled section of the slot.

15. The system of claim 13, wherein when the control button is shifted to the full deployment position, the control button is axially slidable along the axial section of the slot.

16. A method for delivering a self-expanding stent, the method comprising:
advancing a stent delivery system through a body lumen to a position adjacent to a target region;
wherein the stent delivery system includes:
   an inner member having a distal region,
   a stent disposed along the distal region,
   a deployment sheath disposed about the stent,
   a handle coupled to the deployment sheath,
   wherein the handle has a slot formed therein, the slot having an angled section and an axial section;
   a control button movably disposed along the slot in the handle for proximally retracting the deployment sheath,
   wherein the control button is designed to shift axially along the handle between a pre-deployment position and a full deployment position, and
   a force reduction member for reducing the amount of force required for shifting the control button from the pre-deployment position to the full deployment position;
shifting the control button from the pre-deployment position to the full deployment position;
wherein shifting the control button from the pre-deployment position to the full deployment position includes shifting the control button to the axial section of the slot; and
proximally sliding the control button along the handle.

* * * * *